United States Patent
Engqvist et al.

(10) Patent No.: US 7,501,018 B2
(45) Date of Patent: Mar. 10, 2009

(54) CHEMICALLY BONDED BIOMATERIAL WITH TAILORED PROPERTIES

(75) Inventors: Hakan Engqvist, Knivsta (SE); Leif Hermansson, Länna (SE)

(73) Assignee: Doxa AB, Uppsala (SE)

( * ) Notice: Subject to any disclaimer, the term of this patent is extended or adjusted under 35 U.S.C. 154(b) by 65 days.

(21) Appl. No.: 10/533,380

(22) PCT Filed: Dec. 30, 2003

(86) PCT No.: PCT/SE03/02090

§ 371 (c)(1),
(2), (4) Date: Mar. 20, 2006

(87) PCT Pub. No.: WO2004/058194

PCT Pub. Date: Jul. 15, 2004

(65) Prior Publication Data

US 2006/0156959 A1    Jul. 20, 2006

(30) Foreign Application Priority Data

Dec. 31, 2002  (SE) .................................. 0203910

(51) Int. Cl.
*A61K 6/06* (2006.01)
(52) U.S. Cl. .................. 106/35; 424/409; 424/422; 424/423; 623/23.62; 623/23.56; 623/23.61; 106/690; 106/691; 106/695; 106/696; 106/816; 106/814; 106/713; 106/724
(58) Field of Classification Search .......... 206/219; 424/409, 422, 423; 623/23.62, 23.56, 23.61; 106/35, 690–691, 695, 696, 816, 814, 713, 106/724
See application file for complete search history.

(56) References Cited

U.S. PATENT DOCUMENTS

| | | | | |
|---|---|---|---|---|
| 3,536,191 A | * | 10/1970 | Williams | 206/221 |
| 4,182,447 A | | 1/1980 | Kay | |
| 4,362,242 A | | 12/1982 | Cheetham et al. | |
| 4,772,326 A | * | 9/1988 | Heinen et al. | 106/645 |
| 6,620,232 B1 | * | 9/2003 | Kraft et al. | 106/404 |

FOREIGN PATENT DOCUMENTS

| WO | WO 00/21489 | * 4/2000 |
|---|---|---|
| WO | WO 01/76534 | * 10/2001 |
| WO | WO 01/76535 | * 10/2001 |

* cited by examiner

*Primary Examiner*—C. Melissa Koslow
(74) *Attorney, Agent, or Firm*—Birch, Stewart, Kolasch & Birch, LLP

(57) ABSTRACT

A chemically bonded biomaterial element composed of an inorganic cement, exhibiting minimal dimensional changes upon hardening and long-time use, improved mechanical properties and improved translucency. An algorithm to describe the micro-structure is expressed as $$\lambda = \frac{d*(1-V_F)}{(V_F)}$$

where λ is the distance between filler particles of mean size d, and $V_F$ is the volume content of non-reacted cement and added filler, and where $\lambda \leq 10$ μm. The invention also relates to a device in connection with the preparation of a chemically bonded biomaterial element according to the invention.

26 Claims, 2 Drawing Sheets

CHEMICALLY BONDED BIOMATERIAL WITH TAILORED PROPERTIES

TECHNICAL FIELD

The present invention relates to a system for biomaterials for preferably dental or orthopaedic materials, comprising an aqueous hydration liquid and a powdered material that in the main consists of an inorganic cement system, which powdered material has the capacity following saturation with the hydration liquid to form a tailored micro-structure, which results in a very high dimensional stability at the hardening and long-time use of the material, a high strength and optimized optical properties and an advanced micro-porosity. The invention also relates to the powdered material and the hydration liquid, respectively, and a process and preparation for the production of the material.

STATE OF THE ART AND PROBLEM

The present invention relates to binding agent systems of the hydrating cement system type, in particular cement-based systems that comprise chemically bonded ceramics (so called CBC-materials, from the English expression "Chemically Bonded Ceramics") in the group that consists of aluminates, silicates, phosphates, sulphates and combinations thereof, having calcium as the major cation. The invention has been especially developed for biomaterials for dental applications, preferably dental filling materials or root filling materials, and orthopaedic applications, both bone cements and fillers as well as implantation materials including coatings and as carrier materials for drug delivery, preferably as components or as granules, but can also be used as fillers for industrial applications within electronics, micro-mechanics etc.

For materials, such as filling materials as implants, that are to interact with the human body, it is an advantage that the materials are made as bioactive or biocompatible as possible. Other properties that are required for dental filling materials and implants are a good handling ability with simple applicability in a cavity, moulding that permits good modellability, hardening/solidification that is sufficiently rapid for filling work and provides serviceability directly following therapy, high hardness and strength, corrosion resistance, good bonding between filling material and biological wall, dimensional stability, radio-opacity, good long time properties and good aesthetics especially regarding dental filling materials. For the purpose of providing a material that fulfils at least most of these required properties, a material has been developed according to what is presented in SE 463,493, SE 502,987, WO 00/21489, WO 01/76534 and WO 01/76535, e.g.

The present invention relates specifically to the field of dimensional stability (avoiding shrinking or expansion) while maintaining good mechanical, optical and biochemical properties, the object being to provide materials with zero expansion at hardening and long-time use, i.e. the material does not change its outer shape at solidification or long-time use or only marginally changes in outer geometry.

ACCOUNT OF THE INVENTION

The present invention aims at providing biomaterials having a complex property profile, in which focus is on the obtaining of zero expansion and mechanical properties, and thereby to provide a powdered material that is composed of a cement based system that has the capacity following saturation with a liquid reacting with the powdered material to hydrate and chemically react to a chemically bonded material, which material exhibits minimal dimensional changes upon hardening and at continued hydration, hardening and maturing, and for long-time use, i.e. during several years. By zero expansion is meant a material with minimal linear change, or expressed as expansion pressure or tensile force by a definition of the exercised pressure or tension on the surrounding volume, as <5 MPa, <2 MPa, even more preferred <1 MPa. The expansion pressure or tensile force is advantageously measured by a photoelastic method (Ernst et al. Am J Dent 2000; 13:69-72).

Zero Expansion—Phenomena and Controlling of the Same

Dimensional stability within expansion or shrinking areas, is generally controlled by different factors such as
 1. Particle size
 2. Binding agent additives
 3. The degree of compaction
 4. Content of inert materials These are described in earlier patents and patent applications mentioned in the introduction above and in a doctor's thesis (L Kraft, Calcium aluminate based cement as dental restorative materials, Uppsala Universitet, 13 Dec. 2002).

For chemically bonded ceramics of the type calcium-aluminate-hydrate (CAH), calcium-phosphate-hydrate (CPH) and calcium-silicate-hydrate (CSH), the hardening mechanism is dissolving of powdered raw material by reaction with water, formation of ions and deposition/crystallization. A consequence of this is that if the chemically bonded ceramic exists in an entirely or partially closed volume, the deposition can take place on the walls of the volume, which means that expansion is not needed for a tight union. This is shown in embodiment example 2 below. Hereby, no stresses occur in the biological tissue, despite the obtaining of a tight union. In the dental case, this means that secondary caries can be prevented. It is desirable to fill the entire volume without affecting the surrounding walls mechanically, by compressive forces. At mechanical affecting, the surrounding volume may be plastically deformed or may rupture, depending on the size of the expansion force.

Zero expansion can be obtained by maintaining an algorithm that decides the largest deviating micro-structure field, based on mean values built up from the included phases. Zero expansion is expressed as expansion pressure or tensile force by a definition of the exercised pressure or tension on the surrounding volume, as <5 MPa, <2 MPa, even more preferred <1 MPa. This is obtained by minimal dimensional changes.

Mechanical Properties

Strength is controlled by the largest existing defects in materials that are linearly elastic (brittle) by character. The largest deviation in the micro-structure controls the tensile strength ($\sigma$), which is described by the fracture mechanism basic expression $\sigma = 1/Y \times K_{IC}/c^{1/2}$, where c is a maximal defect, $K_{IC}$ is the fracture toughness and Y is a constant. A decreasing amount of pores and a decreasing pore size contributes indirectly to an improved strength, and also to a higher hardness and a higher E-modulus. These said properties are being controlled at the same time as the dimensional stability is controlled in accordance with the present invention.

Micro-Porosity Properties

By controlling the micro-structure according to the present invention, an effect on the porosity is obtained that generally contributes to improved mechanical properties according to the above. Another effect is that micro-porosity may be specifically controlled—to extent as well as to size. The micro-porosity will result from the internal chemical shrinkage. The pore size depends on the general micro-structure, i.e. how large hydrates that can be formed, which in turn depends on the base system that is used, i.e. how fast phases are formed and which phases that are formed. Hereby, the mean distance between existing phases is decisive. Complementing hydrated phases—e.g. apatite phases or other biologically active phases—can result from substances or ions that are added to the hydration liquid. The formation of these phases results in that the hydrated phases of the base system will be limited in extension, and thereby also the size of formed minipores. The size of these pores is, to 90% of the total porosity, below 0.5 μm and may be controlled to a level of 10-100 nm. Controlling the porosity is of fundamental importance in the use of cement based systems, especially the Ca-aluminate system, in applications as carrier material for drug delivery systems. Diffusion in the material takes place by liquid phase in the pore system. The diffusion is controlled by the pore system, that for materials according to the invention is characterised by 1) open porosity, despite the total porosity being below 10%, even more preferred below 5% and most preferred below 2%. The main part of the pores exist as minipores of sizes below 0.5 μm, most preferred below 100 nm (meso-structures). The material may exist as small components or as precompacted granules.

Translucency Properties

The importance of controlling the size of the phases included in the micro-structure according to the present invention is evident from that given in the sections above on controlling of expansion towards zero values, controlling of mechanical properties and porosity. This is of great relevance for materials having optical properties such as translucency—by controlling the end product micro-structure, by minimizing pores within the visible wave length range of 0.4-0.8 μm. The porosity may be controlled to exist as pores having a maximal size of 0.4 μm. The size of included phases is also kept below 0.4 μm or above about 1 μm.

General Description of the Micro-Structure of Chemically Bonded Materials

The micro-structure is composed of:
Binding agent—material that forms hydrates
Non-reacted binding agent
Filler particles
Pores (internal pores and minipores related to chemical shrinkage)

The raw materials are powdered raw material, advantageously in the form of compacted granules, and water, foremost water with small additives of accelerators or agents for controlling consistency and controlling the formed hydrated phases.

Description of the Affect of Micro-Structure on Expansion

The expansion of a chemically bonded material depends on hydrates (reaction products) being formed in a restricted area. Generally, shrinking should take place at hydration in related cement systems, so called chemical shrinking depending on a molar volume contraction taking place at formation of hydrates, which in a non-restrained situation will result in shrinkage. Restricting areas may be an uneven distribution or the raw materials, formation of pockets, an already formed micro-structure that causes a rigid structure. That is, if there is a pore to be filled by hydrate in the vicinity of the cement particle that is being dissolved, the body will not expand. It is also the case that the driving force for a continued dimensional change will decrease as the porosity is filled by hydrate (the body will become more rigid). A fine micro-structure (high specific surface area of the initial powder) will therefore result in a decreased expansion. Consequently, a higher degree of compaction of the raw materials will lower the expansion, as will a compacting pressure on the material itself during the dissolving but before deposition of many enough hydrates for the material to be considered as set. A compacting pressure during the actual period of dissolving (initial setting) will result in the volume that corresponds to the chemical shrinking being eliminated or reduced. The degree of compaction of the material will be additionally increased.

The expansion is controlled by the prerequisites for formation of a fine crystalline, homogeneous micro-structure. The following is of importance: the size and distribution of hydrated phases, the size of the non-reacted cement phases, the size of inert phases (filler particles), the content of included phases, the size and content of pores, the general distribution of all included phases, the initial degree of compaction (a higher degree of compaction will give a finer micro-structure, the w/c ratio), the extent of the initial chemical shrinkage.

The above factors decide the final micro-structure. The extent of the expansion can be summed-up in an algorithm that describes the mean distance between included phases, see FIG. 1 and equation 1. The smaller it is, the less can a single deviating factor affect the expansion. Accordingly, the dimensional stability, strength, optical properties are decided by the largest possible deviation in micro-structure. See FIG. 1.

Figure 1:
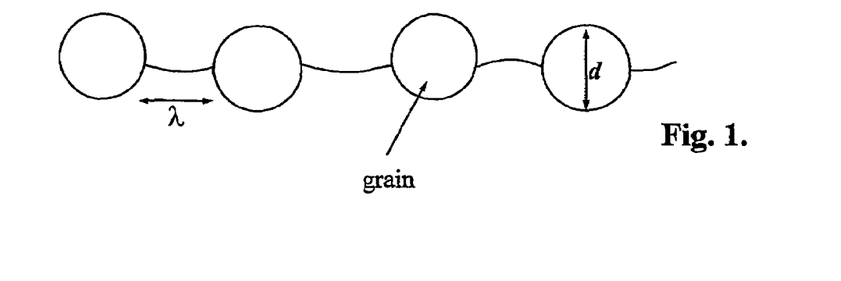
FIG. 1 is a schematic illustration of $\lambda$.

The size of areas possible in the micro-structure, can be described by:

$$\lambda = \frac{d*(1-V_F)}{(V_F)} \quad (1)$$

Where $\lambda$ is the distance between filler particles of mean size d, and $V_F$ is the volume content of non-reacted phases and added inert phases. Accordingly, equation 1 describes the maximal pore size and size of formed hydrates. The mathematical derivation of equation 1 is described in Underwood, E. Quantitative stereology, Addison-Wesley (1970).

A small $\lambda$ will result in a low expansion. Accordingly, this can be controlled by a small filler particle size (also non-reacted cement is regarded as filler in this context, when discussing the hydrated body), and a lower content of hydrates. It is accordingly to be noted that the particle size is the size obtained after dissolution of parts of the cement. A low content of hydrates is achieved by a low water to cement ratio. For practical products, the content of non-hydrated material plus added inert filler particles, should not be above 50% by volume. Suitably, the volume content of non-hydrated material plus added inert filler particles is kept within the range 5-45%, more preferred 15-35%.

Added, inert filler particles should have a mean particle size smaller than 5 μm, even more preferred smaller than 2 μm. They may be composed of e.g. glass particles, apatites, brucite and/or böhmite.

In embodiment example 1, the distance is described as a function of the contents of non-hydrated material in the hydrated body. To reach a low expansion, it should be true that $\lambda \leq 10$ μm, preferably $\lambda \leq 8$ μm, even more preferred $\lambda \leq 4$ μm and most preferred $\lambda \leq 2$ μm. It is easier to reach high $\lambda$-values at lower filler contents. At values of $\lambda > 10$, not only will the expansion become higher, but at the same time problems arise concerning strength and concerning the attaining of a high translucency and/or radio-opacity.

λ denotes the maximal size of a hydrate. It may also be the case that the distance λ is built up from a plurality of hydrate particles of different sizes. Advantageously, ions in the hydration liquid are used, that form complementing hydrates or phases in-situ, which separate the formed hydrates of the main system, i.e. the Ca-aluminate system. Also, the hydration process contributes to the blending of different hydrates and sizes of hydrates, by early formation of hydrates by reaction of Ca-aluminates having a high content of Ca, and by late formation of hydrates by Ca-aluminates having a high content of Al. See below. The hydrates may also exist in the form of amorphous or partly amorphous compositions. Examples of hydrates are: katoite, gibbsite, apatite, other hydrates of calcium-aluminates, calcium silicate hydrates etc. By the mechanisms above, the hydrates will very seldom be critical from a size point of view regarding deviations in the micro-structure, which means that size in equation 1 above is related to filler particles and not to hydrates.

Ca-aluminates of all existing phases can be used as raw material, i.e. pure CaO, $(CaO)_3Al_2O_3$, $(CaO)_{12}(Al_2O_3)_7$, $CaOAl_2O_3$, $(CaO)(Al_2O_3)_2$, $(CaO)(Al_2O_3)_6$ and pure $Al_2O_3$ with varying relative contents. The contents of included phases may vary within wide ranges. The main phases are $CaOAl_2O_3$ and $(CaO)(Al_2O_3)_2$. The most preferred phase is $CaOAl_2O_3$. The content of each of $(CaO)_3Al_2O_3$, $(CaO)_{12}(Al_2O_3)_7$ and $(CaO)(Al_2O_3)_6$ is below 10% by volume, counted on the total content of Ca-aluminate.

The volume mean particle size (d) for the hydrated body, can be described by $$d = \sum_i \alpha_i d_i \quad (2)$$

For αi it is always true that $$\sum_i \alpha_i = \sum_i \frac{V_i}{V_F} = 1 \quad (3)$$

where i corresponds to the number of non-hydrated phases in the hydrated material. αi the part that the phase i occupies of the volume that the non-hydrated phases occupy together, i.e. 0<αi<1 and the sum of all αi is 1. αi relates to the part of the volume ($V_F$) in equation 1 that the phase i occupies. di (volume mean particle size) should preferably be below 10 μm, more preferred below 5 μm, even more preferred below 3 μm, even more preferred below 1 μm and most preferred below 0.5 μm. It is also the case that d99 of each phase should be below 20 μm, suitably below 10 μm (volume based particle size).

For a hydrated calcium aluminate based material, d is described as $$d = \alpha_{C3A}d_{C3A} + \alpha_{C12A7}d_{C12A7} + \alpha_{CA}d_{CA} + \alpha_{CA2}d_{CA2} + \alpha_{CA6}d_{CA6} + \alpha_C d_C + \alpha_A d_A + \alpha_{filler}d_{filler}$$

where C=CaO and A=$Al_2O_3$ and the term filler sums up the added inert phases (glass particles, oxides, initially added apatite etc).

The volume part of hydrates is controlled by the amount of water that is added to the powder blend in relation to the amount of phases that can react and the compacting pressure for the powder-water blend before it has set, and accordingly it will vary depending on the degree of compaction.

It is preferred that a mechanical pressure is applied to the material during an initial reaction, preferably within 5 minutes, even more preferred within 2 minutes and most preferred within 1 minute after the hydration liquid has been added to the raw material.

Expansion compensating agents such as micro-silica and OPC in accordance with the patents mentioned in the introduction, are effective, but at an expansion below 0.2% these agents will be increasingly ineffective as such. In this area, the expansion/dimensional stability is controlled by the algorithm given in the present application.

According to another aspect of the invention, the cement-based systems comprises chemically bonded ceramics in the group that consists of aluminates, silicates, phosphates, sulphates and combinations thereof, preferably having cations in the group that consists of Ca, Sr and Ba. The cement may also comprise one or more expansion compensating additives adapted to give the ceramic material dimensionally stable long-term attributes, as is described in WO 00/21489.

The powdered material, preferably only in the form of granules including optional additives or possibly granules and non pre-compacted powder material according to the above, may, according to yet another embodiment, be mixed with a liquid that reacts with the binder phase, where after the resulting suspension is injected directly into a cavity that is to be filled. Suitably, the liquid comprises water and—in addition to an, together with a component in the powdered material, optional organic forming phase—accelerator, disperser and/or superplasticizer, in order to obtain a suitable consistency of the suspension. The accelerator speeds up the hydrating reaction and is preferably composed of a salt of an alkali metal. Most preferably, a lithium salt is used, e.g. lithium chloride, lithium fluoride or lithium carbonate. The superplasticizer is preferably composed of a lignosulphonate and/or citrate, EDTA and/or hydroxycarboxy containing compounds, PEG or substances with PEG-containing units. Also in the embodiment in which the suspension is drained and compacted, the accelerator, disperser and/or superplasticizer may of course be used, as well as in the embodiment in which the material is compacted to a raw compact, in which case the raw compact is brought to absorb the liquid when the ceramic material is to be produced. The hydration liquid used, to a volume fraction of the total volume of materials within the range of 0.25-0.55 before initial hydration reaction, may also contain ions or ion forming substances that in-situ form apatite or some other phase that separates the formed hydrates of the main system.

In a preferred embodiment, the biomaterial element of the invention also comprises the above organic phase, preferably at a volume content of <5%. Preferably, such phase is composed of polyacrylates and/or polycarbonates.

The time aspect of the hydration is of great importance for the size of the expansion. In addition to by which Ca-aluminates that exist (see above), this also is controlled by the accelerator composition and the content thereof. During an initial stage, the hydrating material exists in a plastic, mouldable stage with a low E-modulus of the paste. This leads to any possible dimensional changes not resulting in high pressures but that a relaxation takes place by an internal change of shape. This is possible inter alia thanks to the dissolution and commencing deposition that takes place initially together with a chemical shrinkage. An internal chemical shrinkage takes place due to the molar volume contraction that is mentioned above. A time span allowed for this plastic time is controlled by aid of accelerator. The time span for plastic deformation according to the above, is controlled in respect of the application, for odontological and orthopaedic applications being less than 30 minutes, preferably less than 20 minutes and most preferred less than 10 minutes. This time span is related to the content of accelerator, which for LiCl corresponds to a content of Li within the range of 30-150 ppm.

The present invention also relates to a system for the production of a chemically bonded ceramic material of a powdered material, the binder phase of which essentially consisting of a calcium based cement system, which system has the capacity to form apatite in-situ. By capacity to form apatite in-situ it is hereby meant that the system comprises the components that are necessary for the formation of apatite, hydroxyapatite or fluoride-apatite (($Ca_5(PO_4)_3OH$ and $Ca_5(PO_4)_3F$, respectively) for example, and optionally some other biologically favourable phase, and that the system allows for such phases to be formed during and/or after the hydration reaction. Apatite formed in-situ separates the Ca-aluminate hydrates of the main system. It is especially preferred that the main binder phase of the cement system consists of calcium aluminate (Ca-aluminate), since:

1. Ca-aluminates will give a basic local environment for the apatite, which makes that phase stable (no dissolution, preventing formation of plaque and lactic acid).
2. Ca-aluminate exists in surplus and is formed in all pores in the material—contributes to fill the material—if only apatite was used for example, too little water would be transformed in order for water-filled porosity to be filled by hydrate.
3. Ca-aluminate is deposited by acid-base reaction, in which water reacts with the powdered material, that starts to dissolve. In the solution, all constituents exist that are needed for the formation of both calcium aluminate hydrate, gibbsite and apatite (if some type of phosphor is supplied) and possibly some other biologically favourable phase (calcite, aragonite, lactate etc.). When the solubility product of each substance is reached, a deposition starts to take place. The deposition takes place everywhere, including inside the micro-spaces between the filling material and the tooth wall. Small crystals are deposited in the surface topography in the tooth wall or some other biological contact surface and contributes to the complete disappearance of the contact zone of filling material-tooth/bone, leading to microstructural integration.
4. In biological liquid system, there are hydrogen phosphates that act as a pH stabilising buffering agent. This aqueous system reacts with basic Ca-cements while forming apatite.

The additive material can also have any morphology or form, including: spheres, regular or irregular forms, fibres, whiskers, plates or the like. Particles of the additive should be smaller than 10 μm, preferably smaller than 5 μm, even more preferred smaller than 2 μm.

Regarding other aspects concerning the method of suspension, reference is made to WO 01/76534, the content of which is incorporated herein by reference. Regarding other aspects of raw compacts, reference is made to WO 01/76535, the content of which being incorporated herein by reference.

In addition to applications such as dental filling materials or orthopaedic compositions, applications within fields such as substrates/casting materials for electronics, micromechanics, optics and within biosensor techniques can be seen.

EXAMPLE 1

Figure 2:
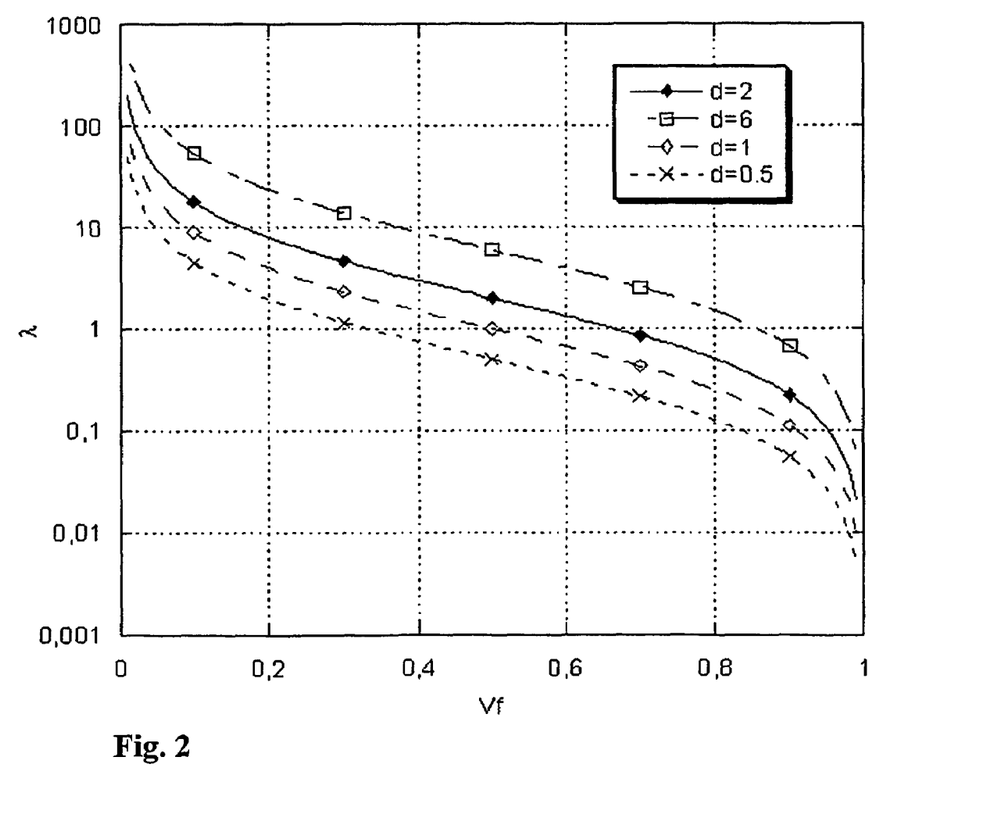
FIG. 2 illustrates the distance $\lambda$ between filler particles of the mean size d as a function of the volume content of inert material $V_F$.

In FIG. 2, $\lambda$ is the distance between filler particles of mean size d (both in μm), and $V_F$ is the volume content of inert material, i.e. non-reacted cement material plus added inert particles. A small $\lambda$ will result in a low expansion. Accordingly, this can be controlled by a small filler particle size (also non-reacted cement is regarded as filler in this context, when discussing the hydrated body), and a small content of hydrates. It is accordingly to be noted that the particle size is the size obtained after dissolution of parts of the cement. A low content of hydrates is achieved by a low water to cement ratio. In FIG. 2, the distance is described as a function of the content of non-hydrated material plus added inert particles in the hydrated body. To reach a low expansion, it should be true that $\lambda \leq 10$ μm, preferably $\lambda \leq 8$ μm, even more preferred $\lambda \leq 4$ μm and most preferred $\lambda \leq 2$ μm.

EXAMPLE 2

Tests were made in order to study the effect of $\lambda$ on hardness, expansion pressure and rigidity in a chemically bonded ceramic material. The expansion pressure is measured by a photoelastic method (Ernst et al. Am J Dent 2000; 13:69-72). In this method, the material is placed in a circular hole in an Araldite plate, and is placed in liquid for hydratisation. In this photoelastic evaluation, one monitors the appearance of Newton rings dependent on any tensions that the material transfers to the Araldite plate through which light is directed. The diameters of the Newton rings are related to the expansion pressure. The samples are stored for a few weeks time, in order to follow the expansion development. After a few days, a maximum pressure has been reached. The measurement is monitored for a few weeks to confirm the maximum pressure.

Trial Series a) hydrated material with $\lambda$4 μm (50% by volume hydrate and 4 μm particle size for phases that are not hydrates)
b) hydrated material with $\lambda$2 μm (50% by volume hydrate and 2 μm particle size for phases that are not hydrates)
c) hydrated material with $\lambda$0.5 μm (50% by volume hydrate and 0.5 μm particle size for phases that are not hydrates)
d) hydrated material with $\lambda$0.3 μm (50% by volume hydrate and 0.3 μm particle size for phases that are not hydrates)
e) hydrated material with $\lambda$11 μm (50% by volume hydrate and 11 μm particle size for phases that are not hydrates)

Production of Material

The materials were produced by mixing water and powder blend at such ratios that the final volume was filled by 50% by volume of hydrate. The method of mixing materials is described below and in FIG. 4. The remaining volume of the hydrated body was then composed of non-hydrate phases (non-reacted cement and inert fillers). The used cement phase was $CaOAl_2O_3$, which gave gibbsite and katoite as hydrate phases (as controlled by X-ray diffraction). The inert filler was a blend of different apatites and dental glass. The material blends were kept in water of 37° C. for 2 weeks before hardness (Vickers hardness), expansion pressure (photoelastic method) and rigidity (E-modulus) were measured. The results are shown in the table below. The particle sizes of the chemically bonded ceramics were measured as the linear intercept particle size in one dimension. Recalculated to three dimensions, the particle sizes and also λ became somewhat bigger (equations according to Fullman).

TABLE 1

| Material | λ (μm) | Hardness (HV0.1) | Rigidity (GPa) | Expansion pressure (MPa) |
|---|---|---|---|---|
| a | 4 | 120 | 15 | 3 |
| b | 2 | 132 | 15.7 | 2.1 |
| c | 0.5 | 146 | 17 | 1.7 |
| d | 0.3 | 151 | 17.6 | 0.9 |
| e | 11 | 100 | 14 | 5.5 |

The results show that a lower λ will give a higher hardness, a lower expansion and a more rigid material.

The method for mixing the materials in trials a-e is described with reference to FIG. 4.

EXAMPLE 3

TABLE 2

Variation of strength with λ and d, strength in MPa. Flexural strength measured by ball on disc method.

| Material having | Diameter d = 6 μm | Diameter d = 4 μm | Diameter d = 2 μm |
|---|---|---|---|
| λ 8 μμ | 58 | 65 | 74 |
| 1 4 mm | 70 | 81 | 92 |
| 1 2 mm | 89 | 102 | 120 |

EXAMPLE 4

TABLE 3

Variation of translucency with λ and d, translucency in %.

| Material having | Diameter d = 6 μm | Diameter d = 4 μm | Diameter d = 2 μm |
|---|---|---|---|
| 1 8 mm | 18 | 23 | 27 |
| 1 4 mm | 25 | 29 | 32 |
| 1 2 mm | 33 | 36 | 42 |

Figure 3:
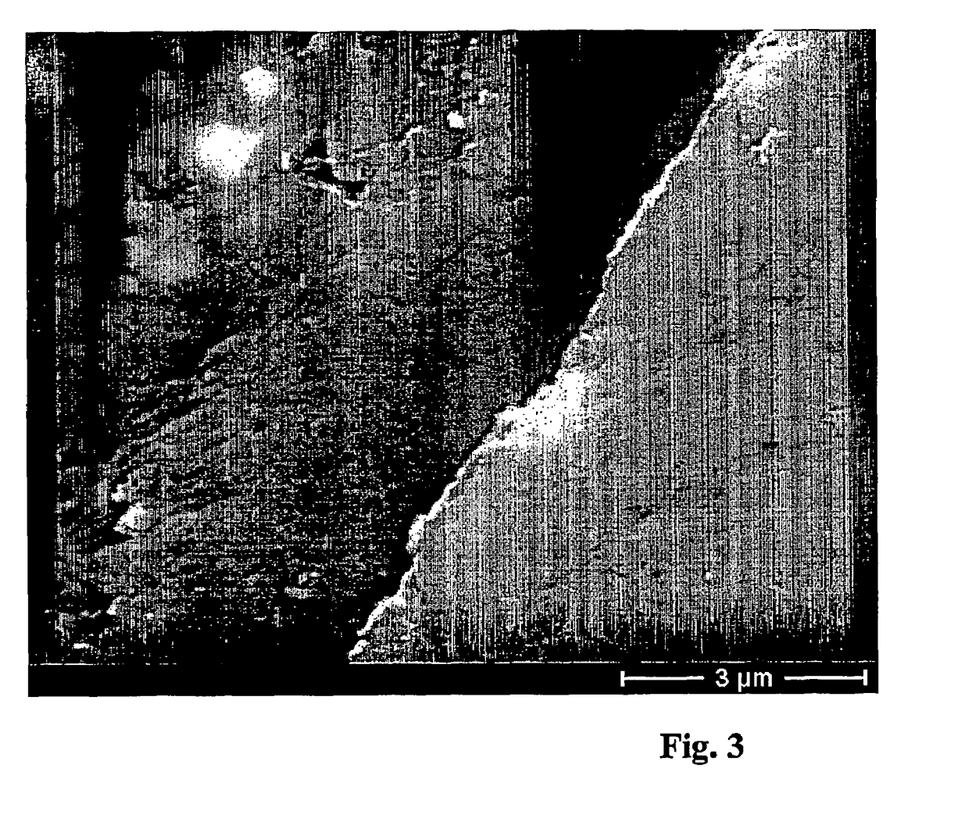
FIG. 3 shows an image of the transition between material and biological wall, where a precipitation of hydrate has taken place on the biological wall.

FIG. 3 shows an image of the transition between material and biological wall, where a precipitation of hydrate has taken place on the biological wall. The area to the left is material with filler particles with λ<1 μm, the area in the middle shows deposition of hydrates at absence of filler particles showing deposition on a biological wall, the area to the right is biological material, in this case enamel. The deposition area in the middle of the image has a thickness of about 2 μm.

Figure 4:
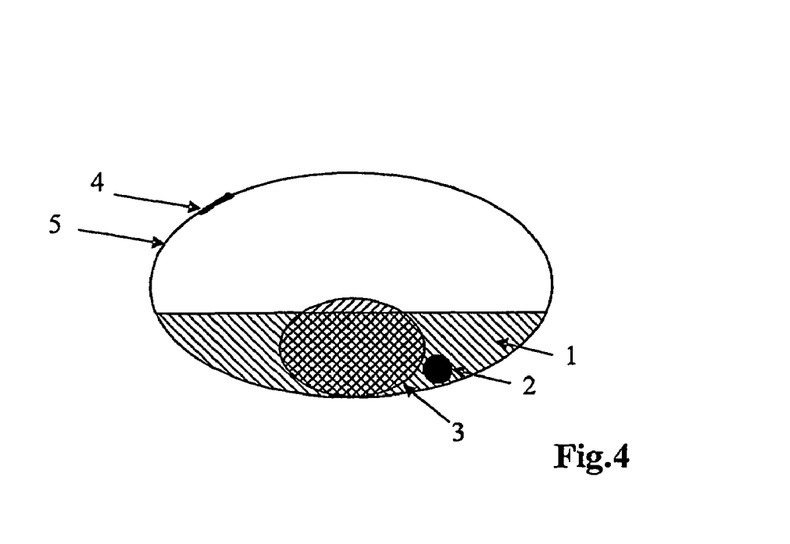
FIG. 4 shows a device for the production of a chemically bonded bioceramics according to the invention.

FIG. 4 shows a device for the production of a chemically bonded bioceramics according to the invention. A powdered blend 1 for the ceramic material is under vacuum in a container 5 having an outer casing of preferably transparent plastics. The hydration liquid is kept in a container 3. An openable closure is arranged between the powder container 5 and the liquid container 3, which closure in the present case is composed by the walls of the liquid container, the liquid container being arranged inside the powder container.

A ball 2 residing in one of the containers and preferably being of ceramic material is vibrated manually or by machine, and then the liquid container 3 is broken and the powdered blend 1 is mixed with the liquid. As the powdered blend is under vacuum in the container 5, the mixing takes place momentarily. When a good mixing and viscosity has been achieved, the suspension is drained via the hole 4 that can be opened from the outside. The suspension is then applied in a volume that is to be filled. Advantageously, the powder exists as granules with a high degree of compaction.

The invention is not restricted to the embodiments shown but can be varied within the scope of the claims.

The invention claimed is:

1. A chemically bonded biomaterial element comprising:
an inorganic cement, exhibiting minimal dimensional changes upon hardening and long-time use, improved mechanical properties and improved translucency;
and added inert filler particles, wherein
the biomaterial element has a micro-structure to meet an algorithm, which is-defined by a formula:

$$\lambda = \frac{d * (1 - V_F)}{(V_F)}$$

where λ is The distance between filler particles of mean size d, and $V_F$ is the volume content of non-reacted cement and the added inert filler particles, and where λ≦10 μm, and
wherein the added inert filler particles have a particle size below 5 μm, and
wherein the added inert filler particles consist of glass particles, apatites, brucite and/or bobmite.

2. The biomaterial element according to claim 1, wherein λ≦8 μm.

3. The biomaterial element according to claim 1, wherein $V_F$ is less than 50%.

4. The biomaterial element according to claim 1, wherein it exerts a pressure or tensile force of <5 MPa on a surrounding volume.

5. The biomaterial element according to claim 1, wherein the inorganic cement comprises Ca-aluminate, Casilicate, Ca-phosphate, or a mixture thereof.

6. A biomaterial element according to claim 1, wherein the inorganic cement comprises $CaO-Al_2O_3$ system, and a particle size of formed hydrates of These phases is below 3 μm.

7. The biomaterial element according to claim 1, wherein the biomaterial element further comprises an organic phase of polyacrylates and/or polycarbonates at a volume content of less than 5%.

8. The biomaterial element according to claim 1, wherein it comprises in-situ formed apatite that separates the formed hydrates of the main system.

9. The biomaterial element according to claim 1, wherein a total porosity is below 10%, where at least 90% of the pores are minipores having a diameter below 0.5 μm.

10. The biomaterial element according to claim 1, wherein it is a dental material.

11. The biomaterial element according to claim 1, wherein it is a component, or is in granule form.

12. The biomaterial element according to claim 1, wherein λ≦4 μm.

13. The biomaterial element according to claim 1, wherein λ≦2 μm.

14. The biomaterial element according to claim 1, wherein $V_F$ is 5-45%.

15. The biomaterial element according to claim 1, wherein $V_F$ is 15-35%.

16. The biomaterial element according to claim 1, wherein it exerts a pressure or tensile force of <2 MPa on a surrounding volume.

17. The biomaterial element according to claim 1, wherein it exerts a pressure or tensile force of <1 MPa on a surrounding volume.

18. The biomaterial element according to claim 6, wherein the $CaO$—$Al_2O_3$ system contains at least one selected from $(CaO)_3Al_2O_3$, $(CaO)_{12}(Al_2O_3)_7$, $CaOAl_2O_3$, $(CaO)(Al_2O_3)_2$, $(CaO)(Al_2O_3)_6$, $CaO$, pure $Al_2O_3$ and a mixture thereof.

19. The biomaterial element according to claim 6, wherein a main phase of the $CaO$—$Al_2O_3$ system is $CaOAl_2O_3$ or $(CaO)(Al_2O_3)_2$.

20. The biomaterial element according to claim 6, wherein a main phase of the $CaO$—$Al_2O_3$ system is $CaOAl_2O_3$.

21. The biomaterial element according to claim 6, wherein a particle size of formed hydrates of these phases is below 1 μm.

22. The biomaterial element according to claim 6, wherein a particle size of formed hydrates of these phases is below 0.5 μm.

23. The biomaterial element according to claim 1, wherein added inert filler particles have a particle size below 2 μm.

24. The biomaterial element according to claim 1, wherein a total porosity is below 5%, distributed on minipores having a diameter below 0.1 μm, to an extent of at least 90% of the total porosity.

25. A biomaterial element according to claim 10, wherein the dental material is a dental filling material or a root filling material.

26. The biomaterial element according to claim 1, wherein it is a carrier material for drug delivery.

* * * * *

UNITED STATES PATENT AND TRADEMARK OFFICE
CERTIFICATE OF CORRECTION

PATENT NO. : 7,501,018 B2
APPLICATION NO. : 10/533380
DATED : March 10, 2009
INVENTOR(S) : Hakan Engqvist et al.

It is certified that error appears in the above-identified patent and that said Letters Patent is hereby corrected as shown below:

In column 9, lines 21-23, delete Table 2 and replace it with the following:

TABLE 2

| Material having | Variation of strength with $\lambda$ and d, strength in MPa. Flexural strength measured by ball on disc method. | | |
|---|---|---|---|
| | Diameter d = 6 μm | Diameter d = 4 μm | Diameter d = 2 μm |
| $\lambda$ 8 μm | 58 | 65 | 74 |
| $\lambda$ 4μm | 70 | 81 | 92 |
| $\lambda$ 2μm | 89 | 102 | 120 |

UNITED STATES PATENT AND TRADEMARK OFFICE
CERTIFICATE OF CORRECTION

PATENT NO. : 7,501,018 B2
APPLICATION NO. : 10/533380
DATED : March 10, 2009
INVENTOR(S) : Hakan Engqvist et al.

It is certified that error appears in the above-identified patent and that said Letters Patent is hereby corrected as shown below:

In column 9, lines 31-46, delete Table 3 and replace it with the following:

TABLE 3

| Variation of translucency with $\lambda$ and d, translucency in %. | | | |
|---|---|---|---|
| Material having | Diameter d = 6 μm | Diameter d = 4 μm | Diameter d = 2 μm |
| $\lambda$ 8 μm | 18 | 23 | 27 |
| $\lambda$ 4μm | 25 | 29 | 32 |
| $\lambda$ 2μm | 33 | 36 | 42 |

Signed and Sealed this

Second Day of June, 2009

JOHN DOLL
*Acting Director of the United States Patent and Trademark Office*